United States Patent [19]

Barrada

[11] 4,280,508
[45] Jul. 28, 1981

[54] METHOD FOR POSITIONING A FLUID WITHDRAWING MEANS BY DETECTING LOCAL TEMPERATURE

[76] Inventor: M. Ismail Barrada, 45 E. Pleasant Lake Rd., North Oaks, Minn. 55110

[21] Appl. No.: 107,542

[22] Filed: Dec. 27, 1979

[51] Int. Cl.³ ............................................. A61B 10/00
[52] U.S. Cl. .................................... 128/736; 128/760; 128/765; 128/214.4; 73/352
[58] Field of Search ............... 128/736, 763, 765, 760, 128/770, 774, 775, 778, 771, 347, 630, 664; 73/352

[56] References Cited

U.S. PATENT DOCUMENTS

| | | |
|---|---|---|
| 2,321,846 | 6/1943 | Obermaier . |
| 2,407,288 | 9/1946 | Kleimack et al. . |
| 2,816,997 | 12/1957 | Conrad . |
| 2,970,411 | 2/1961 | Trolander . |
| 3,054,397 | 9/1962 | Benzinger . |
| 3,094,122 | 6/1963 | Gauthier et al. .................. 128/214.4 |
| 3,254,533 | 6/1966 | Tongret . |
| 3,339,542 | 9/1967 | Howell . |
| 3,489,137 | 1/1970 | Marchal et al. . |
| 3,704,705 | 12/1972 | Eckhart . |
| 3,889,658 | 6/1975 | Newhall . |
| 3,951,136 | 4/1976 | Wall . |
| 3,971,362 | 7/1976 | Pope et al. . |
| 4,175,567 | 11/1979 | Patel ................................. 128/774 X |

FOREIGN PATENT DOCUMENTS 233160 10/1969 U.S.S.R. .
264607 6/1970 U.S.S.R. .
312608 11/1971 U.S.S.R. .

OTHER PUBLICATIONS

"YSI Thermistor Probes", Yellow Springs Instrument Co., Inc., Scientific Div., Yellow Springs, Ohio, 45387.
"Instructions for YSI Series 500 Temperature Probes", Yellow Springs Instrument Co., Yellow Springs, Ohio, 45387.
Hill et al., Obstetrics and Gynecology, vol. 49, p. 236, 1977.
Creasman et al., J. Amer. Med. Asso., vol. 204, p. 91, 1968.
Robinson et al., Am. J. Obstet. Gynecol., vol. 116, p. 937, 1973.
"Amniocentesis," Contemp. Ob/Gyn, vol. 5, pp. 59–64, May 1975.

*Primary Examiner*—Kyle L. Howell
*Attorney, Agent, or Firm*—Merchant, Gould, Smith, Edell, Welter & Schmidt

[57] ABSTRACT

A method for withdrawing a sample of enclosed fluid from an internal organ of a living mammal by using a temperature-sensitive probe to reliably position a fluid withdrawing means into the fluid containing organ. In particular, a method for detecting a change in temperature in the myometrium tissue during penetration of a cannula into a uterus to minimize the possibility of injury to a fetus in an amniocentesis procedure.

6 Claims, 6 Drawing Figures

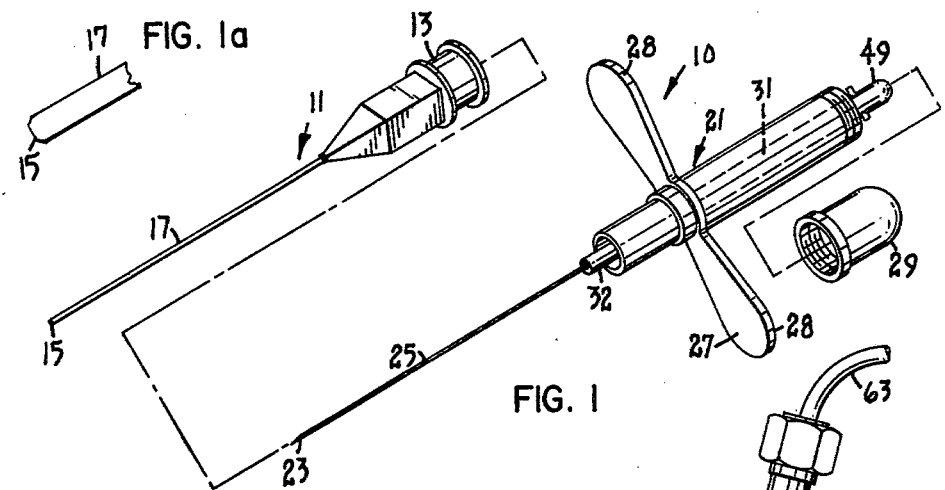
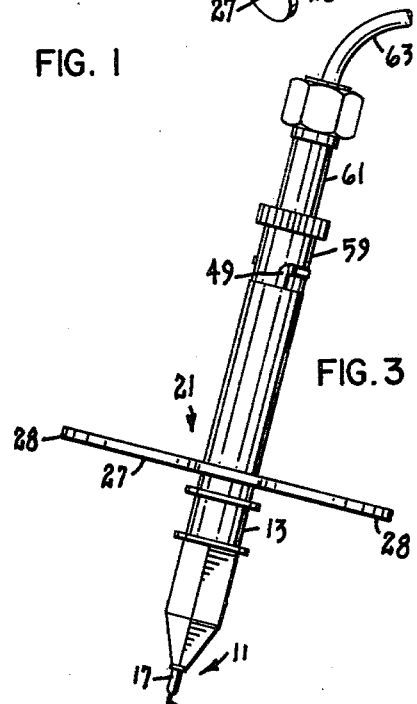
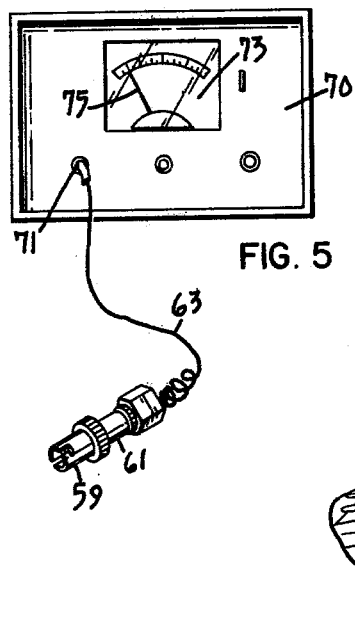
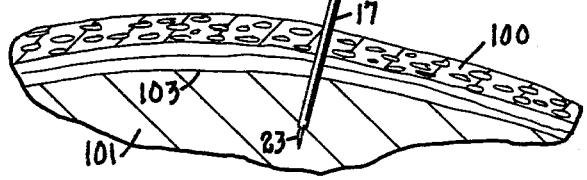
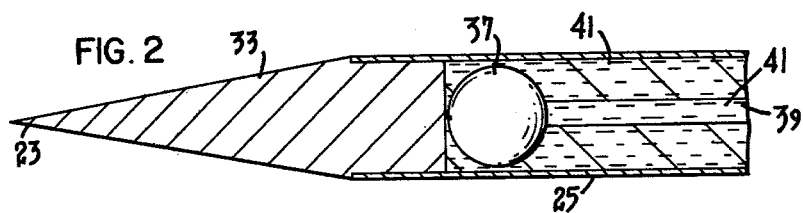

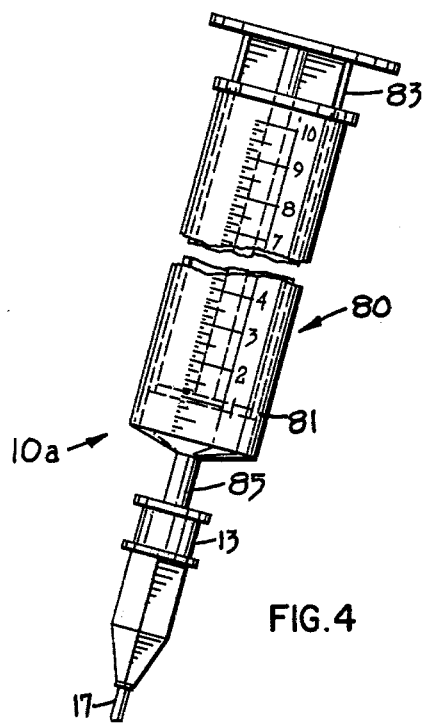
FIG.4
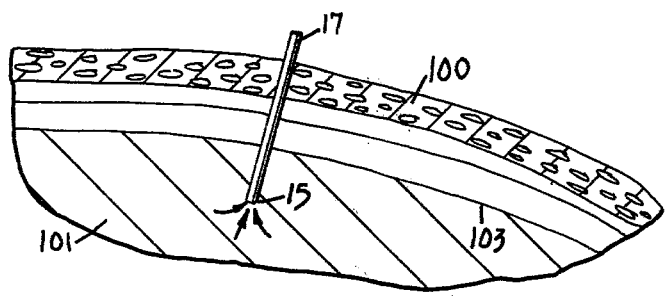

METHOD FOR POSITIONING A FLUID WITHDRAWING MEANS BY DETECTING LOCAL TEMPERATURE

FIELD OF THE INVENTION

This invention relates to a medical diagnostic procedure having tissue-penetrating and fluid-withdrawing functions. An aspect of this invention relates to a method for penetrating into an internal fluid-filled cavity of a living mammal and withdrawing fluid from that cavity. An important aspect of this invention relates to the procedure termed amniocentesis.

BACKGROUND OF THE PRIOR ART

A common practice in many medical diagnostic procedures is to penetrate into some portion of a living mammal with a hollow needle or cannula through which tissue or fluid can be withdrawn. Amniocentesis is an example of such a procedure.

Amniocentesis was first suggested more than 90 years ago. Following up on this suggestion, physicians were able to relieve an overdistended uterus by tapping some of the amniotic fluid. Still later, it was discovered that amniotic fluid could be used for diagnostic purposes, e.g. in studies of Rh-sensitized women, assessment of fetal maturity, antenatal diagnosis of genetic disorders (including chromosomal abnormalities, inborn errors of metabolism, congenital malformations, etc.), determination of fetal sex, and the like. The procedure has been used particularly in the second and third trimesters of pregnancy. In the second trimester, it is typically carried out for the diagnosis of genetic disorders and to determine the sex of the fetus, whereas in the third trimester, fetal maturity studies and Rh factor determination are perhaps the most common indications for the procedure.

Transabdominal amniocentesis is currently carried out with the aid of a standard 19 or 20 gauge, 7-10 cm spinal needle which consists of a stylus fitted into a hollow cannula. Selection of the appropriate site for amniocentesis depends primarily on determination of the fetal lie by manual palpatation of the abdomen, and is further facilitated by an ultrasound examination for localization of the placenta and an accessible pocket of fluid. The spinal needle is advanced through the different layers of the abdomen, through the muscular wall of the uterus, and entry into the amniotic sac is typically recognized by the sudden loss of resistance to the forward progress of the needle. The stylus is then withdrawn, a syringe attached to the hub of the needle, and amniotic fluid is aspirated.

Despite the simplicity of the procedure and the increasing use of ultrasonics to facilitate the localization of the placenta, failures as well as complications to the fetus continue to occur as a result of the procedure. Literature has appeared which suggests the possibility of a number of minor as well as very serious complications. For example, see Creasman et al, "Fetal Complications of Amniocentesis", JAMA, 204:91 (1968), and Robinson et al, Am. J. Obstst. Gynecol., 116:937 (1973).

One of the inconveniences of the procedure occurs in the case of a "dry tap". For reasons which are not clearly understood, it occasionally happens that fluid cannot be aspirated, even though the distal end of the needle is inside the amniotic sac. Unfortunately, it can be difficult to distinguish a dry tap from a situation in which the needle has not yet penetrated the sac. A dry tap indicates that another puncture site should be selected, while a failure to penetrate the sac indicates that advancement of the needle should be continued. For both patient and practitioner, it would be a great convenience if dry taps could be recognized quickly and reliably.

In an article by Hill et al, Obstetrics and Gynecology, 49:236 (February, 1977) it has been suggested that the adaptation of the spring-loaded needle which is currently being used in laparoscopy to induce pneumoperitoneum, could reduce the likelihood of fetal complications. The authors report that virtually every part of the fetus has been struck by needles used for amniocentesis. In an effort to reduce fetal morbidity and mortality, Hill et al adapted a spring-loaded needle for amniocentesis, whereby the sudden movement of an inner trocar would signal penetration into the amniotic sac, thereby obviating further advancement of the needle.

Although improvements in the amniocentesis procedure have been developed and are still being developed, any further improvement for decreasing the failure rate and particularly the risk of fetal complications will be a welcome contribution, especially in view of the fact that the procedure is becoming more widespread in the practice of obstetrics.

SUMMARY OF THE INVENTION

It has now been discovered that the gradient in temperature between the structure of the uterus itself (i.e. the myometrium) and the amniotic fluid can be utilized to reliably determine entry into the amniotic sac in an amniocentesis procedure. Although this invention is not bound by any theory, it is believed that organs such as the uterus of a pregnant mammal which enclose a fluid have an inherent tendency to develop a temperature difference between the wall of the organ and the interior reservoir of fluid. Apparently, the fluid in the interior of the organ acts as a heat sink and is not able to effectively dissipate heat through the wall of the organ, perhaps because of a thermal insulation effect. As a result, the temperature of the fluid (e.g. amniotic fluid) tends to climb slightly and reach a reasonably stable level which is higher than the temperature of the wall. In human amniocentesis studies, it has been found that the difference in temperature between the myometrium and the interior of the amniotic sac can be on the order of at least 0.1° C., more typically about 0.2° to about 0.8° C. Temperature differences on the order of 0.25° C. or higher are observed with most patients.

It has further been discovered that this temperature difference can be used to add an extra dimension of safety to the amnoicentesis procedure, provided that the increase in temperature which should be observed upon entering the amniotic sac can be detected with sufficient swiftness and accuracy.

As is known in the art of electronics, a temperature-sensing material can be included in an electrical circuit, and readings from an electrical measuring device in the circuit can be correlated with temperature changes. The temperature-sensing material can be, for example, a thermistor or the combination of materials often referred to as a thermocouple. Such electrical or electronic temperature-measuring circuits can measure temperatures in the 35°-45° C. range to an accuracy of ±0.2° C., an accuracy to ±0.1° C. or less being preferred. In the case of a thermistor, approximately 100% of the temperature change is sensed and responded to within about 10 to 20 time constants. (Thermistor temperature probes having time constants ranging from less than 0.1 second up to 7 seconds or more are commercially available; the short time constant probes are preferred, so that an accurate reading can be obtained in a few seconds.)

Although this invention is applicable to any medical diagnostic method which involves invasive penetration into an enclosed pocket of fluid within a living mammal and withdrawal of a sample of the fluid, the most important field of use of the invention is in amniocentesis. In many other fields of use, infection, internal bleeding, and puncturing of an internal organ not being diagnosed are perhaps the greatest dangers associated with the procedure. In amniocentesis, however, there is the additional and very real danger that a fetus may be severely harmed. Furthermore, it has been found that the amniotic sac and the fluid which it contains are a remarkable heat sink, storing up significantly more heat than the surrounding tissues, as noted previously. To carry out a procedure according to this invention, the following steps are carried out.

(a) the outer wall of a fluid-containing internal organ is invasively contacted through subcutaneous penetration with the distal end of a cannula means (e.g. transabdominal penetration into the wall of the uterus), or a cannula/stylet combination (the stylet can do double duty as a temperature probe);

(b) the temperature of the outer wall of the organ—which outer wall now contacts or surrounds the distal end of the cannula means—can now be measured with a temperature-sensing probe inserted into the cannula means;

(c) penetration into the organ is continued while retaining the temperature-sensing probe in its inserted position within the cannula means, and temperature measurements can be made during this further penetration;

(d) further penetration is stopped when the temperature measurement obtained according to step (c) increases by at least about 0.1° C. (in the case of amniocentesis, this temperature increase indicates penetration of the amniotic sac);

(e) the temperature-sensing probe is removed, so that a sample of the fluid (e.g. amniotic fluid) can be withdrawn; and (f) withdrawal of the fluid through the passageway provided by the cannula means can then be carried out, e.g. by aspirating with a syringe.

A device suitable for carrying out the foregoing procedure comprises:

(a) a cannula having a hub at the proximal end, which hub is constructed and arranged to engage a fluid-aspirating device such as a syringe;

(b) a temperature-sensing probe which can function as a stylet and can be inserted into the cannula means and which has a suitable electrical connection at its proximal end;

(c) an electrical device for measuring temperature which can be connected to the electrical connection at the proximal end of the stylet/temperature probe; and (d) a suitable fluid aspirating device such as a syringe, which is constructed and arranged to enter into a fluid-tight engagement with the hub of the cannula.

Thus, this combination of elements is designed to be assembled into an invasive mode, wherein the stylet/temperature probe is inserted through the hollow cannula, so that the tissue can be invaded and its temperature taken in a manner similar to the use of the hypodermic resistance thermometer for measuring local temperatures described in U.S. Pat. No. 2,816,997 (Conrad), issued Dec. 17, 1957. In addition, a medical diagnostic device of this invention can be disassembled (i.e. the stylet/probe withdrawn) and reassembled (the aspirating syringe or the like engaged with the cannula hub) while the cannula is held in place in the desired region of the body. For convenience, disposable parts of the medical diagnostic device of this invention can be packaged in a sterilized tray.

BRIEF DESCRIPTION OF THE DRAWING

FIG. 1 is an exploded perspective view of a diagnostic device of this invention including the cannula and stylet/temperature-sensing probe of this invention;

FIG. 1A is an enlarged fragmentary view of the distal end of the cannula;

FIG. 2 is an enlarged fragmentary cross-sectional view of the distal end of the stylet/temperature-sensing probe;

FIG. 3 is a perspective view of the device of FIG. 1 in use with parts of the body of the patient shown in cross-section;

FIG. 4 is a perspective view similar to FIG. 3 with the device of FIG. 1 reassembled for aspiration of fluid and with the same parts of the patient's body shown in cross-section; and FIG. 5 is a perspective view showing electrical connection, circuit, and temperature-measuring means constructed and arranged to electrically connect with the device of FIG. 1.

DETAILED DESCRIPTION

Since the method of this invention involves both non-surgical invasion of tissue and a fluid-withdrawing step, the medical diagnostic devices used in the practice of this invention are capable of carrying out both functions. The device has component parts capable of being assembled for the invasive mode or configuration of the device and for the fluid sampling (e.g. aspiration) mode or configuration. The elements most important to the invasive configuration are the cannula means and the stylet/temperature-sensing probe, which probe is provided with electrical or electronic means for comparing a current flow to a set of standards for current flow, so that temperature can be read electrically or electronically. For the fluid-sampling configuration, the most important element is a fluid-withdrawing device such as a syringe capable of entering into a fluid-tight engagement with the proximal end of the cannula means, e.g. the conventional barrel-and-plunger syringe. The functions of a stylet and a temperature-sensing probe need not be combined into a single element, but such a combination is greatly preferred. Among the less preferred alternatives is the use of a cannula means with a sharpened distal tip (in which case the probe need not have a sharpened distal end or point) and the alternating use of a stylet and a temperature probe. The former is disadvantageous because of the tendency for the sharpened cannula to make the first contact with the internal bodily fluid, thereby possibly delaying a temperature response in the temperature measuring equipment and possibly increasing the danger of penetrating too deeply into the fluid. The latter is disadvantageous because of the inability to continuously read temperature as the diagnostic device is advanced through the wall of the organ into the fluid.

To minimize the risks of the diagnostic procedure, the temperature-sensative probe should be both accurate and extremely rapid in sensing changes in temperature within the normal range of mammalian body temperatures (e.g. 35°–45° C.). Fortunately, commercially available temperature-sensing probes tend to be very accurate in this temperature region, and the optimum accuracy with such instruments is often obtained over an even larger span of temperatures, e.g. 0°–80° C. Hypodermic thermistor probes are available which have been specifically designed to measure mammalian body temperatures and will provide accurate temperature readings in less than 60 seconds. Depending upon the time constant of the probe, accurate readings in less than 5 seconds or even 1 second are also readily obtainable with existing instruments. Some of these instruments are based upon the thermocouple principle, while others are based upon thermistor technology. A "thermistor" is in essence a resistor made of temperature-sensing material. That is, the electrical resistance of the thermistor varies with temperature and can have either a negative temperature coefficient (in which case the resistance decreases with increasing temperature) or a positive temperature coefficient (wherein resistance increases with increasing temperature). In accordance with solid state technology, the thermistor can be a diode which has an extremely steep resistance versus temperature curve, so that minor changes in temperature will produce dramatic changes in the resistance of the temperature-sensing material. The thermistor need not be located directly at the distal tip of the diagnostic device, so long as the temperature at the tip is thermally transmitted with sufficient speed and accuracy to a circuit including the thermistor. However, it is generally the case that more accurate results will be obtained when the thermistor is located as close to the distal tip of the device as is reasonably possible.

As noted previously, hypodermic resistance thermometers adapted to measure local body temperatures are known in the art. In the resistance thermometer described in U.S. Pat. No. 2,816,997 (Conrad), issued Dec. 17, 1957, a thermistor bead with associated circuitry and electrical insulation is located in the bore of a sealed-end, sharpened needle very close to the sealed point of the needle.

The conventional circuitry used in association with the thermistor to provide accurate temperature measurement is also shown in the U.S. Pat. No. 2,816,997. As shown in this patent, the thermistor bead can be one of the resistances in a leg of a Wheatstone bridge. The galvanometer means (e.g. a current measuring device) in the bridge circuit can be calibrated in temperature units, because of the correlation between temperature and resistance. Thermistor standardizing or calibrating procedures have been known in the art for quite some time, as illustrated by U.S. Pat. No. 2,970,411 (Trolander), issued Feb. 7, 1961. For an example of thermistor probes designed for precision body temperature measurement, see the trade literature of Yellow Springs Instrument Co., Inc., Scientific Division, Yellow Springs, Ohio, e.g. the pamphlet "YSI Thermistor Probes".

The use of electrical circuit means to connect the medical diagnostic device to a remote electrical or electronic unit provided with the galvanometer means for giving a direct read-out of temperature as a function of resistance is particularly desirable, since it limits the number of elements which have to be present in the sterile field. Thus, although the temperature-responsive means which includes the galvanometer means is part of the medical diagnostic device by virtue of the electrical connections and circuitry, it is sufficiently remote from the field to be utilized in a non-sterile condition.

As noted previously, the distal end of the cannula means can be sharpened to eliminate or reduce the need for a sharpened stylus, but it is preferred that the stylus be used and the end of the cannula be blunt. A blunt cannula provides even greater assurance that fetal injury will be obviated during aspiration of amniotic fluid.

When utilizing the principles of this invention in the field of amniocentesis, the sample of amniotic fluid withdrawn from the patient's uterus is employed in any of the conventional diagnostic techniques. Furthermore, so-called dry taps are detected immediately or virtually immediately with a medical diagnostic device of this invention. If the practitioner penetrates beyond the first initial contact with the uterine wall and then observes a sharp increase in temperature on the order of 0.2° C. or greater, he has a reasonably reliable indication that he has entered the amniotic sac. If fluid cannot be withdrawn by aspiration, he then knows that he has made a dry tap, and removal of the device, re-siting, and repeating of the procedure is warranted rather than further penetration. It is believed that risk to the fetus is greatly reduced by the ability to detect dry taps with this degree of certainty.

In recent years, it has become a common practice to prepare pre-sterilized kits containing some or all of the instruments or elements or materials necessary or desirable for a particular medical procedure. In one prior art practice, the materials are placed in a tray-like device which is enclosed within a gas-permeable wrap and sterilized by autoclaving or, more typically, ethylene oxide sterilization. Medical devices of this invention are readily adapted to organization into kit form and tray packaging. For an example of this sterile tray approach, see U.S. patent application Ser. No. 873,389, filed Jan. 30, 1978, now U.S. Pat. No. 4,153,160 and U.S. Pat. No. 3,467,247, the disclosures of which are incorporated herein by reference.

Turning now to the Drawing, wherein like numerals denote like parts in the various views, FIG. 1 illustrates the invasive mode of an amniocentesis device of this invention in exploded perspective. Thus, in this mode, amniocentesis device 10 comprises a cannula means 11 and a stylet/thermistor probe device 21. Cannula means 11 is similar in structure to a spinal needle and can be 5 to 15 centimeters in overall length. It is preferred, however, that the distal end 15 of cannula means 11 (see also FIG. 1A) be blunt rather than sharpened to reduce the risks of the procedure. On the other hand, the dimensions of cannula means 11 can be very similar to those of a spinal needle; for example, the fine hollow cylindrical portion 17 of cannula means 11 can be 19-gauge thin-wall hollow needle stock. Since distal end 15 of cannula means 11 is blunt, the penetration of tissue is effected by the distal end 23 of stylet/thermistor probe 21 (see also FIG. 2). A portion of the stylet/thermistor probe 21 comprises thinwall hypodermic stock 25 which is six to fifteen centimeters in length, i.e. approximately the same length as cannula means 11, except that it is preferred that the thinwall hypodermic stock 25 is long enough to protrude slightly from distal end 15 of cannula means 11, whereby the sharp distal tip 23 of the stylet/thermistor probe 21 projects beyond distal end 15 to provide the tissue penetrating action. Hypodermic stock 25 has a lesser diameter than that of cannula means 11 and hence will make a snug axial longitudinal fit within thinwall stock 11. For example, hypodermic stock 25 can be made from 22-gauge needle stock. To provide a sharpened distal tip or end 23, a flat-cut end of thinwall hypodermic stock 25 has been fit and sealed with a solid metal tip or point 33 (of FIG. 2) comprising a metal such as stainless steel which is suitable for tissue penetration and which can be sharpened repeatedly. Indeed, the physical properties of the metal tip 33 are such that it can be sharpened by the user 10 or 20 times or more without wearing away the metal to the point where the thermistor bead 37 would be damaged. (In the event that the stylet/thermistor probe 21 is intended to be disposable, this repeated sharpening will not be required; however, it is still desirable to use stainless steel or the like to make the solid metal tip 33.) Thermistor bead 37 is preferably located in very closely spaced relationship to end or point 23, although to provide accurate electrical sensing of temperature, electrical insulation 41 does provide an insulating barrier between thermistor bead 37 and metal tip 33. The distance between tip or point 23 and thermistor bead 37 is nevertheless quite small, and conduction of heat through metal tip 33 occurs rapidly, so that thermistor bead 37 essentially senses the temperature at point 23 with essentially no time lag. In addition, the time constant of thermistor bead 37 and its associated circuitry 39 is very short, as described previously. Electrical insulation 41 also insulates thermistor bead 37 and circuitry 39 from the metal hypodermic stock 25.

Stylet/thermistor probe 21 includes a handle means 27 to provide leverage for the practitioner carrying out the procedure. This handle means is particularly well suited to a slow but decisive penetration of the tissue into the myometrium and beyond (distally) into the amniotic sac. The wings 28 on handle means 27 enable the practitioner to control the rate of advance of the stylet/thermistor probe 21 by facilitating the application of relatively constant manual pressure, transmitted through handle means 27. Handle means 27 is particularly useful when the amniocentesis track is first anesthetized with xylocaine or the like using a very fine needle (not shown), e.g. a 22-gauge hypodermic needle. If the needle track or amniocentesis track is not first anesthetized, it is generally expedient to insert the cannula 11/stylet/thermistor probe 21 combination rather rapidly. The circuitry 39 (of FIG. 2) follows the length of hypodermic stock 25 all the way up to the proximal end of stylet/thermistor probe 21. Circuitry 39 provides an electric circuit means for connecting thermistor bead 37 into a Wheatstone bridge circuit which includes reference resistors (not shown) whose electrical resistance is known precisely. The circuitry 39 (FIG. 2) near the proximal end of stylet/thermistor probe 21 (FIG. 1) is contained within a housing 31 which can also contain one or more of the aforementioned reference resistors, if desired. The distal end 32 of this housing 31 resembles the tip of an aspirating syringe in its dimensions, so that it can form a tight engagement with hub 13 of cannula means 11. Hub 13 can be, for example, a Luerloc fitting (e.g. ANSI standard Z 70.1), which is typically either made from stainless steel or brass, the brass being typically chrome-plated. When distal end 32 of housing 31 is engaged in the hub 13, the tip or point 23 of the stylet/thermistor probe 21 protrudes slightly beyond distal end 15 of cannula means 11, as described previously, and the resulting cannula/stylet/thermistor probe combination can function as a unit capable of invading tissue or fluid and measuring the temperature throughout the invasive procedure. At the extreme proximal end of this combination of elements, a cap 29 houses a male jack 49 which serves as an electrical connection means capable of mating with female receptacle 59 (FIG. 5). Female receptacle 59 (which is sterilizable) in electrical connection means 61 is connected electrically to temperature-responsive electrical device 70 via an electric circuit means including cable 63 (which is also sterilizable). Of course, virtually all of the elements discussed so far (i.e. the elements of the cannula means/stylet/thermistor probe combination) are sterilizable either by autoclave techniques or sterilizing gas or both. To provide a combination of elements which is sterilizable in an autoclave, none of the aforementioned elements—even those enclosed within the thinwall hypodermic stock 25—should be adversely affected by temperatures in excess of 100° C., e.g. 100°-200° C. For gas sterilization, these elements should be resistant to any adverse effects resulting from contact with sterilizing gases such as ethylene oxide, and those elements which would not come into contact with the field or the sterilizing gas need not even meet this requirement.

It is ordinarily desirable that cable means 63 be removably connected by means of removable electrical connection means 61 to the temperature-responsive electrical device 70. FIG. 5 illustrates a connection 71 for cable means 63 which permits removal or unplugging of one end of the cable 63. Since cable means 63 may cross the sterile field, it is desirable to permit its segregation from the temperature-responsive electrical device 70, thereby obviating the need to sterilize device 70. The needle 75 on the face of temperature meter 73 is essentially a galvanometer needle which is deflected in response to current flow. Temperature-responsive electrical device 70 has been calibrated in accordance with the correlation between current flow and temperature, so that the face of meter 73 can be read in terms of degrees Celsius rather than milliamperes or microamperes. The full scale of deflection of meter 73 need not encompass more than about 10 Celsius degrees, e.g. 35° C.-45° C. If desired, the full scale deflection can be extended to 30°-50° C. The patient can have a slight fever during the procedure, and this has little or no adverse effect upon the desired temperature measurements; the essence of the procedure is to measure temperature differences rather than absolute temperatures. It has been found that the temperature of the myometrium is typically less than 38.23° C., while the temperature within the amniotic sac is typically greater than this, e.g. 38.3° C. or higher.

Essentially the only major element of an amniocentesis device of this invention which has not already been described is the means for withdrawing fluid, e.g. a syringe-type aspiration device 80 (FIG. 4) which will be described in connection with the manner of use of the device.

FIGS. 3 and 4 relate to this manner of use, i.e. the amniocentesis procedure. FIG. 3 shows the device 10 in use in its invasive mode. The distal end of device 10 has penetrated the abdominal wall 100 and the amniotic sac 103 and has thus reached a pocket of amniotic fluid 101. At this point in its use, the thermistor 37 (FIG. 2) will have detected the higher temperature of the amniotic fluid 101, and the practitioner will have observed a 0.1°

C. or greater deflection of needle 75. Accordingly, the practitioner knows that the amniotic sac has been penetrated and fluid can be aspirated. The stylet/thermistor probe 21 is disengaged from hub 13 (FIGS. 1 and 3) and is removed from device 10. In accordance with a reassembling step described previously, the device 10 is held in position so that there is no further distal movement and no lateral movement of cannula means 11. A syringe-type aspiration device 80 is then used to provide the fluid-withdrawing mode of the device; the resulting reassembled device 10a is shown in FIG. 4. The distal tip 85 of aspiration device 80 is now in fluid-tight engagement with hub 13 of cannula means 11. Aspiration device 80 contains the conventional fluid-tight piston 81 which is integral with a conventional cruciform plunger 83. Retraction of the plunger 83 results in withdrawal of amniotic fluid 101, as indicated by the arrows near distal end 15 of cannula means 11.

Ordinarily, if the procedure is done correctly, the amniotic fluid 101 drawn into aspiration device 80 will be essentially clear and well-suited to various tests and analyses, e.g. analysis for bilirubin. If the sample of fluid thus withdrawn is excessively cloudy or bloody, aspiration device 80 can be disengaged and discarded, a second aspiration device inserted into hub 13, and a new sample drawn. When a satisfactory sample has been obtained, device 10a is withdrawn, and the puncture site covered with a bandage.

I claim:

1. A method for withdrawing a sample of enclosed fluid from an internal organ of a living mammal which encloses said fluid, said method comprising the steps of:
   (a) subcutaneously penetrating into an outer wall of said internal organ with the distal end of a cannula means such that said distal end is in contact with said outer wall;
   (b) measuring the temperature of said outer wall at said distal end with a temperature-sensing probe inserted into said cannula means;
   (c) penetrating further into said organ while retaining said temperature-sensing probe in its inserted position within said cannula means and continuing to measure the temperature surrounding the distal end of said cannula means;
   (d) stopping any further penetration when the temperature measurement obtained according to said step (c) increases by at least about 0.1° C.;
   (e) removing said temperature-sensing probe from said cannula means; and
   (f) withdrawing said sample of fluid from said internal organ through said cannula means.

2. An amniocentesis procedure comprising the steps of:
   (a) inserting a cannula means through the abdomen of a living mammal at least until the distal end of said cannula means is in contact with the wall of the uterus of said mammal;
   (b) measuring the temperature of the portion of myometrium tissue of the wall of said uterus which surrounds the distal end of the cannula means by means of a temperature-sensing probe inserted into said cannula means;
   (c) penetrating into said uterus with the distal end of said cannula means while retaining said temperature-sensing probe in its inserted position within said cannula means and continuing to measure the temperature of said uterus with said temperature-sensing probe;
   (d) stopping penetration with said cannula when the temperature measurement obtained according to said step (c) increases by at least about 0.1° C.;
   (e) removing the temperature-sensing probe from said cannula means; and
   (f) withdrawing a sample of amniotic fluid from said uterus through said cannula means.

3. An amniocentesis procedure comprising the steps of:
   (a) inserting a temperature-sensing probe having a temperature-sensing element at its distal end into a cannula through the proximal end of said cannula, whereby said temperature-sensing element becomes located adjacent to the distal end of said cannula and a cannula/temperature-sensing probe combination is obtained;
   (b) inserting said cannula/temperature-sensing probe combination until it contacts the wall of the uterus and measuring the temperature of said wall;
   (c) further inserting said cannula/temperature-sensing probe combination a distance of at least about one centimeter until a measurement of the temperature of the myometrium of the uterus can be obtained;
   (d) continuing to insert said cannula/temperature-sensing probe combination until the temperature measured adjacent to the distal end of said cannula increases, in less than 5 seconds, by about 0.2° C. to about 0.8° C. above the previously measured temperature of the myometrium;
   (e) ceasing insertion of said cannula/temperature-sensing probe combination and retaining the position of said cannula means fixed while removing said probe and attaching a fluid-aspirating device to the proximal end of said cannula means; and
   (f) aspirating amniotic fluid from said uterus with said fluid-aspirating device.

4. Amniocentesis procedure according to claim 3 wherein the distal end of said cannula means is blunt, and the distal end of said temperature-sensing probe has a sharp point for penetrating tissue.

5. Amniocentesis procedure according to claim 4 wherein said distal end of said temperature-sensing probe includes a thermistor means.

6. Amniocentesis procedure according to claim 4 wherein said sharp point of said probe extends beyond said distal end of said cannula means during said steps (a) through (d).

* * * * *